United States Patent [19]

Goodstein

[11] Patent Number: 5,282,820
[45] Date of Patent: Feb. 1, 1994

[54] LIPOSCULPTURE DEVICE AND METHOD

[76] Inventor: Wallace A. Goodstein, 436 N. Roxbury Dr., S. Penthouse, Beverly Hills, Calif. 90210

[21] Appl. No.: 970,809

[22] Filed: Nov. 3, 1992

[51] Int. Cl.⁵ .............................................. A61B 17/32
[52] U.S. Cl. ................................. 606/170; 604/19; 604/22; 604/902
[58] Field of Search ................. 604/22, 27, 35, 902, 604/19; 606/1, 160, 166, 167, 169, 170, 180, 171, 172

[56] References Cited

U.S. PATENT DOCUMENTS

| | | |
|---|---|---|
| 3,721,244 | 3/1973 | Elmaleh . |
| 3,955,579 | 5/1976 | Bridgman . |
| 4,250,892 | 2/1981 | Dolhay et al. . |
| 4,311,140 | 1/1982 | Bridgman . |
| 4,627,834 | 12/1986 | Lee . |
| 4,735,605 | 4/1988 | Swartz . |
| 4,815,462 | 3/1989 | Clark . |
| 4,850,354 | 7/1989 | Burleson et al. ............... 606/180 |
| 4,857,045 | 8/1989 | Rydell ................................ 604/22 |
| 4,886,491 | 12/1989 | Parisi et al. . |
| 4,932,935 | 6/1990 | Swartz . |
| 4,959,049 | 9/1990 | Smirmavl ......................... 604/22 |
| 4,966,584 | 10/1990 | Nguyen ............................ 604/902 |
| 5,013,300 | 5/1991 | Williams .......................... 604/902 |
| 5,019,088 | 5/1991 | Farr ................................... 606/180 |
| 5,123,903 | 6/1992 | Quaid . |
| 5,181,907 | 1/1993 | Becker ............................. 604/902 |

*Primary Examiner*—Stephen C. Pellegrino
*Assistant Examiner*—Glenn Dawson
*Attorney, Agent, or Firm*—Rothwell, Figg, Ernst & Kurz

[57] ABSTRACT

A tissue-sculpting device includes a tube having an aperture at a distal end of the tube, the aperture extending along a side portion of the tube. At least a portion of the aperture is defined by a fixed, sharpened knife edge for cutting tissue and directing the cut tissue into the tube. A fixed support bridge prevents tissue which is adjacent the tissue being cut from entering the aperture. In the method of the invention, the distal end of the tissue-sculpting tube is moved through fatty tissue so as to cut the fatty tissue with the knife edge, and direct the cut fatty tissue into the tube, thereby removing the cut fatty tissue from the animal's body.

19 Claims, 1 Drawing Sheet

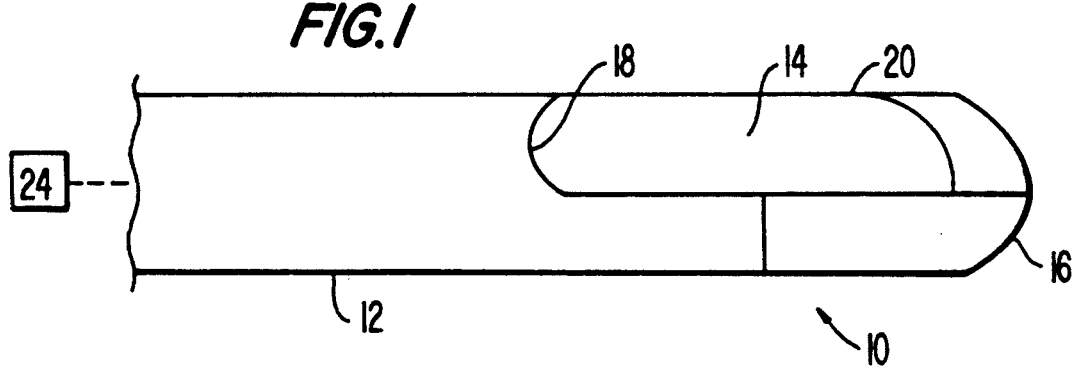
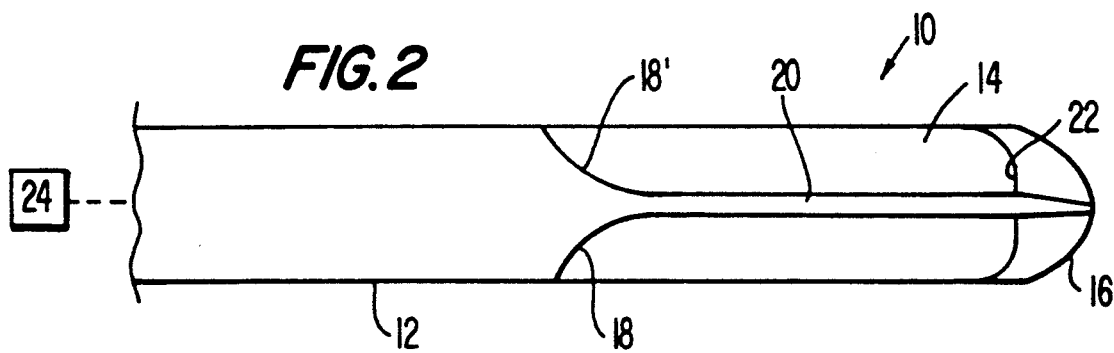
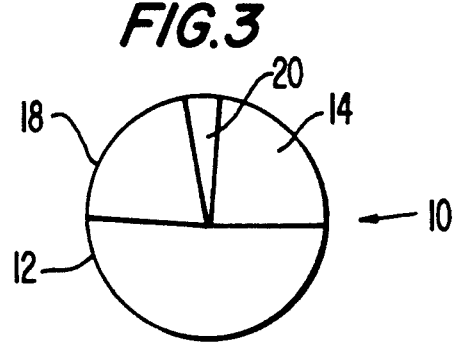

LIPOSCULPTURE DEVICE AND METHOD

BACKGROUND OF THE INVENTION

1. Field of the Invention

The present invention relates to the field of cosmetic surgery.

2. Description of the Background Art

Liposuction surgery has become a common method for removing subcutaneous fat in order to alter body contours. However, it has heretofore generally been accepted that liposuction surgery could only be done safely and effectively by removing the subcutaneous fat relatively deep with respect to the undersurface of the skin, utilizing blunt instrumentation and high pressure suction aspirators.

Suction removal that depends on high negative pressure is by its very nature random, since tissue adherence of subcutaneous fat varies considerably in any given area. Furthermore, the high negative pressures associated with liposuction surgery often severely traumatize adjacent tissue, resulting in substantial blood loss, massive post-operative bruising, severe swelling, and long healing time. Additionally, the random fatty tissue removal resulting from liposuction surgery frequently results in post liposuction irregularities, which often require corrective surgery.

There remains a need in the art for new devices and methods for removing fatty tissue without the high blood loss and other disadvantages resulting from conventional liposuction surgery.

SUMMARY OF THE INVENTION

In accordance with the present invention, a tissue-sculpting device comprises a tube having an aperture at a distal end thereof, the aperture extending along a side portion of the tube. At least a portion of the aperture is defined by a fixed, sharpened knife edge for cutting tissue and directing the cut tissue into the tube. A fixed support is provided for preventing tissue which is adjacent the tissue being cut from entering the aperture.

In the method of the invention, the above-defined device is inserted into fatty tissue of an animal's body, and the distal end thereof is moved through the fatty tissue so as to cut the fatty tissue with the knife edge and direct the cut fatty tissue into the tube, thereby removing the cut fatty tissue from the animal's body.

BRIEF DESCRIPTION OF THE DRAWINGS

FIG. 1 is a side elevational view, somewhat schematic, of a liposculpture device in accordance with the present invention.

FIG. 2 is a top elevational view, somewhat schematic, of the liposculpture device shown in FIG. 1.

FIG. 3 is an end elevational view, somewhat schematic, of the liposculpture device shown in FIGS. 1 and 2.

DETAILED DESCRIPTION OF THE PREFERRED EMBODIMENTS

The figures illustrate a tissue sculpting device 10, which is useful for cutting and removing body tissue, particularly fatty tissue, in accordance with one embodiment of the invention.

The device 10 is comprised of a tube 12 having an aperture 14 at a distal end 16 thereof. In the embodiment shown in FIGS. 1 and 2, aperture 14 extends along a side portion of tube 12, with the distal end 16 of tube 12 being at least partially closed.

As shown in FIG. 3, aperture 14 extends approximately half way around tube 12. In the embodiment shown in FIG. 2, aperture 14 is approximately three times longer than it is wide.

In the embodiment shown, a fixed support bridge 20 is provided for preventing tissue such as dermis, which is adjacent the fatty tissue being cut, from entering aperture 14.

As shown in FIG. 2, bridge 20 bisects aperture 14. In the embodiment shown, a pair of fixed, sharpened knife edge portions 18, 18' are provided on opposite sides of bridge 20 for cutting fatty tissue. It can be seen that the knife edge portions 18, 18' together define a proximal portion of aperture 14. As shown in FIG. 2, adjacent knife edge portions 18, 18' are curved.

Bridge 20 extends longitudinally along tube 12 between the proximal portion of aperture 14 and the distal end portion 22 of aperture 14, which is also at the distal end 16 of tube 12.

In the method of the present invention, a tissue-sculpting device as described above is inserted into fatty tissue of an animal's body.

The distal end 16 of the tube is moved through the fatty tissue so as to cut the fatty tissue with the knife edge portions 18, 18', and direct the fatty tissue into tube 12. The thus-cut fatty tissue is thereby removed from the animal's body through tube 12.

The fatty tissue is cut during advancing movement of the distal end of tube 12 through the fatty tissue. Following an advancing stroke, the tube can be partially withdrawn and the distal end of tube 12 repeatedly advanced through the fatty tissue to continue removal of fatty tissue from the body until the surgery is completed.

In order to facilitate advancement of the tip of tube 12 through the fatty tissue, tube 12 advantageously is sufficiently rigid to permit repeated and controlled advancing strokes through the tissue. One material of suitable rigidity from which tube 12 can be formed is surgical stainless steel.

In preferred embodiments, tube 12 has an external diameter of from about 2 mm to about 25 mm, most preferably less than about 10 mm. In particularly preferred embodiments, tube 12 has an external diameter of from about 3 mm to about 9 mm, more preferably of from about 4 mm to about 8 mm, still more preferably of from about 5 mm to about 7 mm, and most preferably about 6 mm.

In accordance with one embodiment, optional suction means 24, preferably of low negative pressure, can be provided to facilitate removal and clearing of cut tissue from tube 12. The low negative pressure suction which can optionally be utilized with the present invention can be provided, for example, by an inexpensive wall suction unit commonly available in physician's offices.

The present invention provides a valuable new device and method for removing fatty tissue from a body without the need for subjecting the tissue to high negative pressure. The invention permits removal of large amounts of subcutaneous fat from both deep and superficial body areas, eliminating the need for expensive, high-pressure aspirators. Fatty tissue removal can be accomplished without the use of suction, or optional low negative pressure suction can be utilized merely to facilitate clearing of the tube, as opposed to pulling fatty tissue into the tube as with conventional liposuction.

Because the present invention does not rely on high negative pressure to remove fat, the fat removal is considerably more accurate and less random than when utilizing liposuction. The increased accuracy and efficiency of subdermal fat removal resulting from the present invention enhances post-operative results because thorough and homogeneous removal of subdermal fat allows for more uniform skin retraction. Eliminating the need for subjecting the tissues to high negative pressures marketedly reduces blood loss, and aspirate obtained by utilizing the present invention consistently has a dramatically higher fat to blood ratio than that obtained by use of currently available liposuction equipment. Because high negative pressures are not transmitted to the tissues with the present invention, tissue trauma is demonstrably reduced, thus favorably effecting post-operative bruising, swelling and healing time.

Since many modifications, variations and changes in detail may be made to the described embodiments, it is intended that all matter in the foregoing description and shown in the accompanying drawings be interpreted as illustrative and not in a limiting sense.

I claim:

1. A tissue-sculpting device comprising a tube having an aperture at a distal end of the tube, which aperture extends along a side portion of the tube;

at least a portion of said aperture being defined by a sharpened knife edge fixed to said tube, for cutting tissue and directing the cut tissue into said tube; and support means fixed to said tube for preventing tissue which is adjacent the tissue being cut from entering the aperture, wherein the support means comprises a bridge which extends longitudinally along said tube between a proximal portion of said aperture and a distal end portion of said aperture.

2. The device of claim 1 wherein said tube is rigid.

3. The device of claim 1 wherein said knife edge defines a proximal portion of said aperture.

4. The device of claim 3 wherein said bridge substantially bisects said aperture.

5. The device of claim 4 wherein said device includes adjacent knife edge portions on opposite sides of said bridge, which adjacent knife edge portions together define the proximal portion of said aperture.

6. The device of claim 5 wherein said adjacent knife edge portions are curved.

7. The device of claim 6 wherein said bridge extends from said proximal portion of said aperture to the distal end of the tube.

8. The device of claim 1 wherein said tube has an external diameter of from about 2 mm to about 25 mm.

9. The device of claim 8 wherein said tube has an external diameter of from about 2 mm to about 10 mm.

10. The device of claim 9 wherein said tube has an external diameter of from about 3 mm to about 9 mm.

11. The device of claim 10 wherein said tube has an external diameter of from about 4 mm to about 8 mm.

12. The device of claim 11 wherein said tube has an external diameter of from about 5 mm to about 7 mm.

13. The device of claim 12 wherein said tube has an external diameter of about 6 mm.

14. The device of claim 1 further including means connected to a proximal end of said tube for removing cut tissue from said tube.

15. The device of claim 14 wherein the means for removing cut tissue from said tube comprises means for applying suction to said tube.

16. A method for sculpting tissue, comprising:

(a) inserting a tissue-sculpting device into fatty tissue of an animal's body, the device comprising a tube having an aperture at a distal end of the tube, which aperture extends along a side portion of the tube; at least a portion of said aperture being defined by a sharpened knife edge fixed to said tube, for cutting tissue and directing the cut tissue into said tube; and support means fixed to said tube for preventing tissue which is adjacent the tissue being cut from entering the aperture wherein the support means comprises a bridge extending longitudinally along said tube between a proximal portion of said aperture and a distal end portion of said aperture; and (b) moving the distal end of said tube through said fatty tissue so as to cut said fatty tissue with said knife edge and direct the cut fatty tissue into said tube, thereby removing the cut fatty tissue from the animal's body.

17. The method of claim 16 wherein said knife edge defines a proximal portion of said aperture, and wherein said fatty tissue is cut during advancing movement of the distal end of said tube through said fatty tissue.

18. The method of claim 17 wherein said tube is rigid, the bridge substantially bisects said aperture, and the device includes adjacent knife edge portions on opposite sides of said bridge, which adjacent knife edge portions together define the proximal portion of said aperture, and further comprising the steps of repeatedly advancing the distal end of said tube through said fatty tissue so as to remove cut fatty tissue from said body.

19. The method of claim 16 further including the step of applying suction to said tube to remove cut fatty tissue from said tube.

* * * * *